United States Patent [19]

Schulman et al.

[11] 4,197,850

[45] Apr. 15, 1980

[54] IMPLANTABLE HUMAN TISSUE STIMULATOR WITH MEMORY PROTECT MEANS

[75] Inventors: Joseph H. Schulman, Los Angeles; Jozef I. Kie Sioe Tan, Sylmar, both of Calif.

[73] Assignee: Pacesetter Systems, Inc., Sylmar, Calif.

[21] Appl. No.: 957,410

[22] Filed: Nov. 3, 1978

[51] Int. Cl.² .............................................. A61N 1/36
[52] U.S. Cl. ....................... 128/419 PG; 128/419 PS
[58] Field of Search ....... 128/419 P, 419 PG, 419 PS, 128/419 PT

[56] References Cited

U.S. PATENT DOCUMENTS

| | | | |
|---|---|---|---|
| 3,885,572 | 5/1975 | Chen | 128/419 PS |
| 4,024,875 | 5/1977 | Putzke | 128/419 PG |
| 4,096,866 | 6/1978 | Fischell | 128/419 PG |
| 4,120,307 | 10/1978 | Jirak et al. | 128/419 PT |
| 4,124,031 | 11/1978 | Mensink et al. | 128/419 PG |

*Primary Examiner*—William E. Kamm
*Attorney, Agent, or Firm*—Freilich, Hornbaker, Wasserman, Rosen & Fernandez

[57] ABSTRACT

In an implantable human tissue stimulator with a volatile memory an arrangement is provided to protect against the stimulating circuitry producing pulses as a function of unknown parameters in the memory, as a result of inadequate power to the memory from a rechargeable power source, e.g. a rechargeable battery. The arrangement includes voltage sensors, so that when the voltage from the battery drops below a selected level the stimulating circuitry is disconnected from the battery and only the memory is powered. If the voltage from the battery first drops, so that insufficient power is supplied to the memory and thereafter rises, as a result of recharging, to a level sufficient to power the memory, the memory is first reset with known parameter values. Only thereafter when the voltage level reaches the selected level, is the rest of the circuitry, including the stimulating circuitry, reconnected to the battery.

8 Claims, 3 Drawing Figures

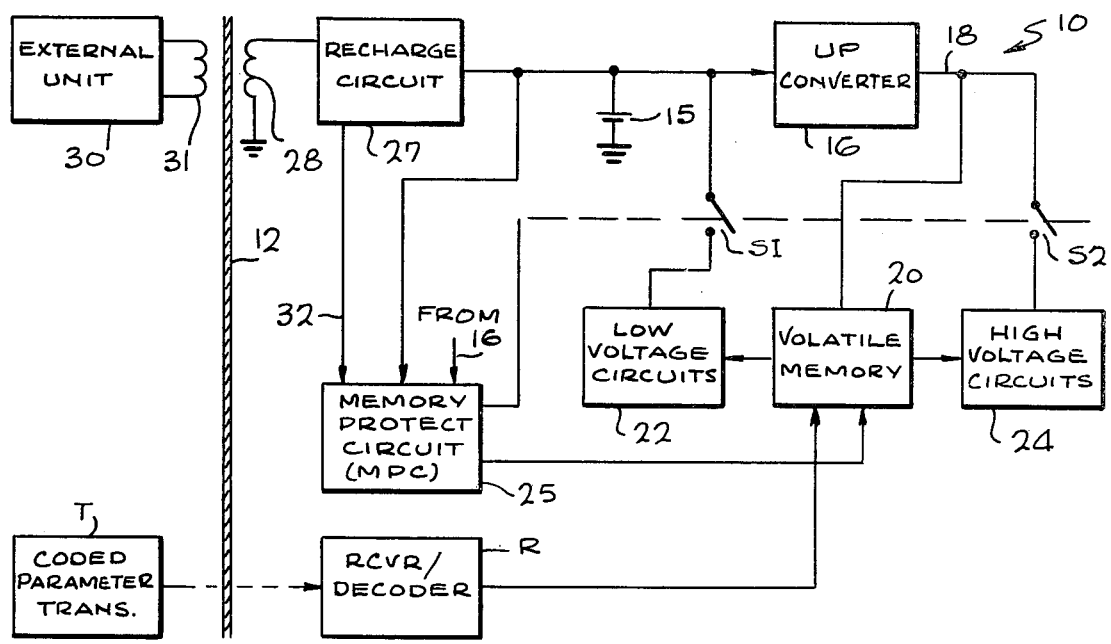
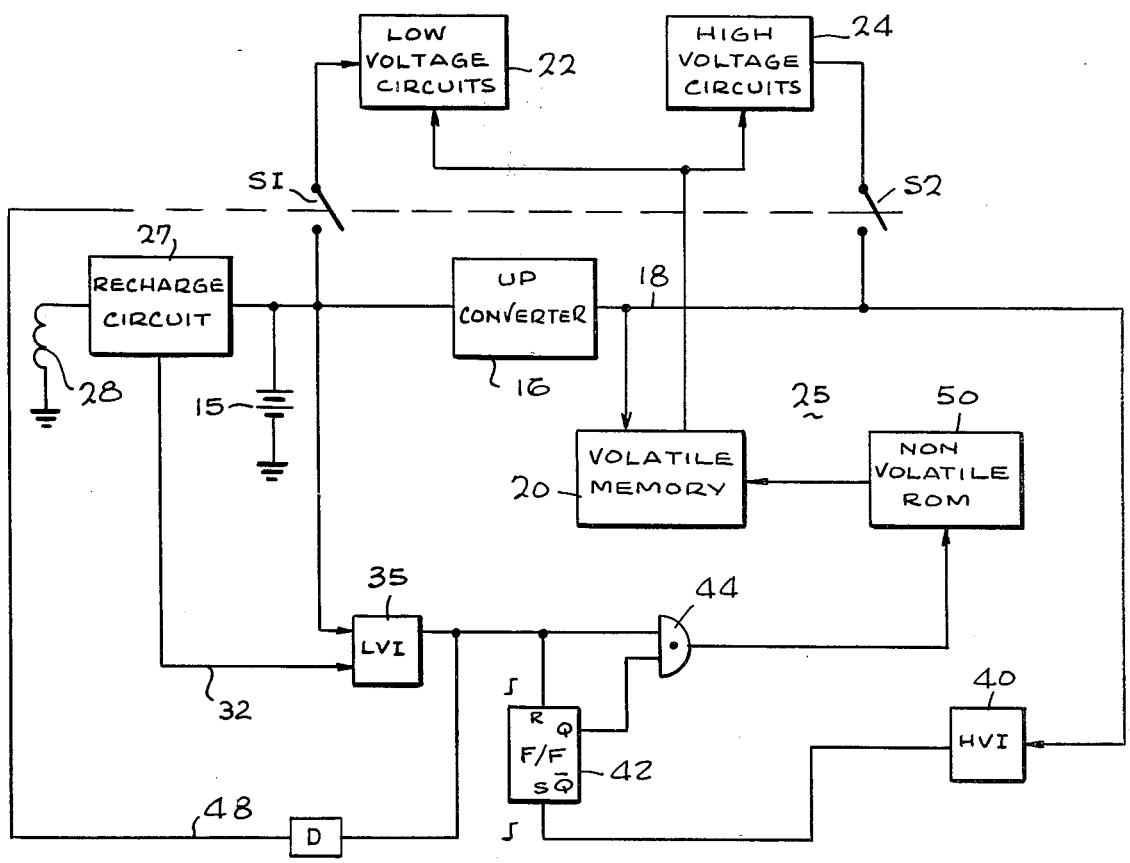

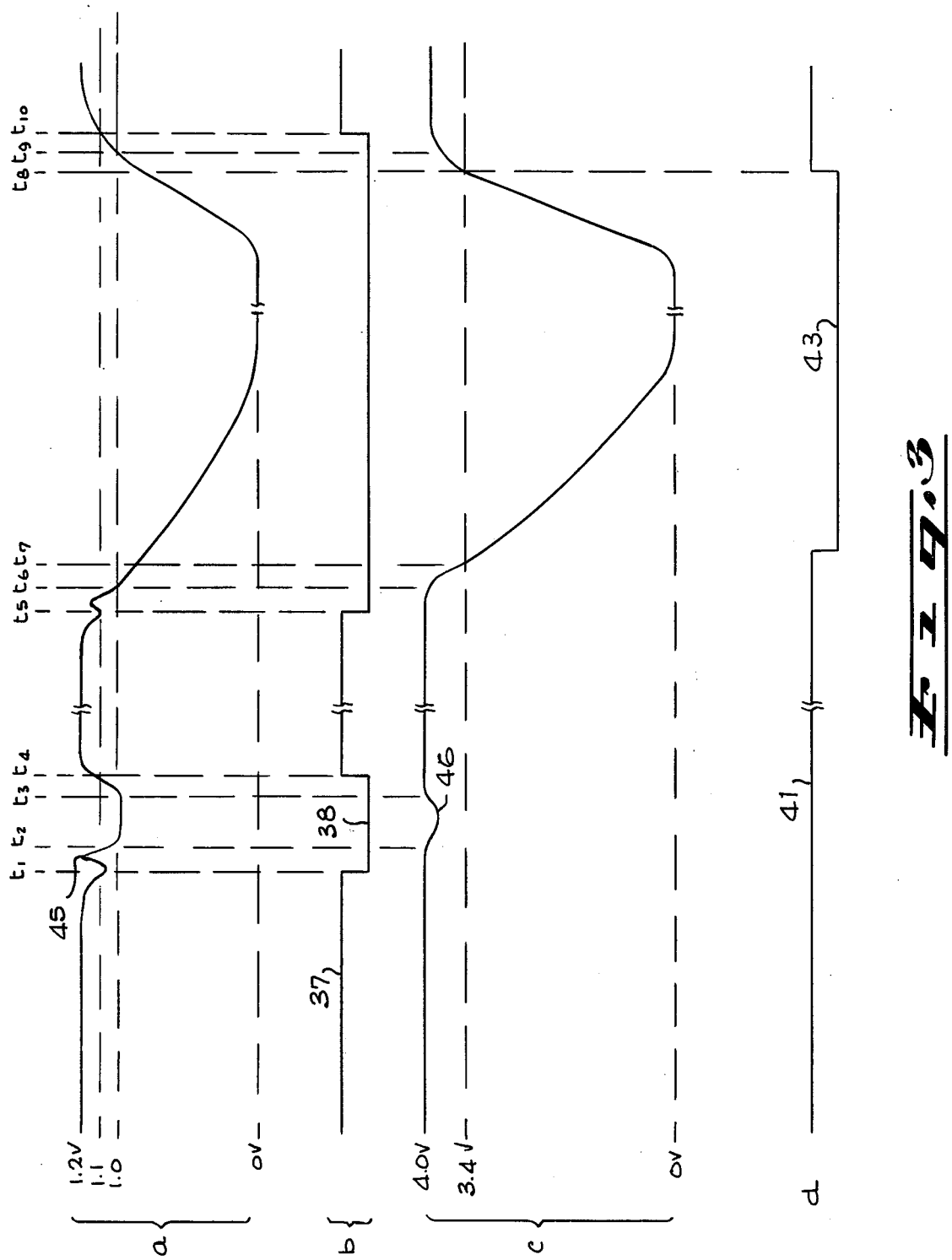

IMPLANTABLE HUMAN TISSUE STIMULATOR WITH MEMORY PROTECT MEANS

BACKGROUND OF THE INVENTION

1. Field of the Invention

The present invention generally relates to living tissue stimulators and biotelemetry devices and, more particularly, to a living tissue interacting device of the type that includes a power source, which powers circuitry and a memory in which parameters for controlling the operation of the circuitry are stored.

2. Description of the Prior Art

Various devices are presently in existence which are implantable in a human patient to stimulate and/or detect signals from body tissues. Among the best known of these devices is the cardiac pacemaker, which provides stimulating pulses to a patient's heart and detects endocardial potentials, via one or more electrodes, which are connected to the pacemaker through electrode leads. Some of the existing implantable cardiac pacemakers include a power source in the form of a battery, which is rechargeable by means of recharging power, transmitted to the implanted pacemaker from an external power source.

In recent years extensive research has been directed to develop stimulators and signal detectors for other than the heart, in order to relieve patients of the crippling effects of various physiological disorders. For example, stimulators and signal detectors have been proposed to stimulate and detect signals from the brain, the spine, muscles, glands and organs or any other tissue. The detected signals and the stimulating pulses from these devices are intended to help patients suffering from various disorders, e.g., cerebral palsy, spasticity, rigidity, epilepsy and other disorders, which are due to either improper, or the absence of, natural stimulating pulses. The detected signals are either used to control the stimulation and/or to inform the doctor of the status of the tissue. Also, it has been appreciated that pain, such as phantom limb pain, resulting from a severed limb, may be alleviated by applying stimulating pulses to the nerves proximal to the damaged area. A workshop was held at the National Institute of Health, Bethesda, Md. on Apr. 27-28, 1972, and a report of the workshop entitled "Functional Neuromuscular Stimulation" was published in 1972 by the National Academy of Sciences, Washington, D.C.

Different disorders require different stimulations. For example, the various properties or characteristics of the stimulating pulses, such as pulse amplitude, pulse frequency, pulse width, and other pulse properties have to be different for different disorders. Also, they may differ from patient to patient. Furthermore, even for the same patient, the pulses' properties may have to be varied, depending on the patient's condition at any given time. Clearly, it would be prohibitively expensive to fabricate a customized stimulator and signal detector for each patient. Furthermore, even if tailor-made for a specific patient, the stimulator would have to be capable of varying the pulses' properties in order to vary the stimulation and to vary the characteristics of the signal detector to suit the patient's changing conditions.

The only practical solution is to provide an implantable stimulator and signal detection system, hereinafter referred to as a human tissue stimulator or HTS, with a programmable memory in which multibit words, hereinafter referred to as parameters, are storeable. At least some of these parameters may be used to control different properties of the stimulating pulses and the signal detector. By varying one or more of the parameters in the memory, different properties of the stimulating pulses and the signal detector may be changed. Any one of the parameters in the memory may be changed by transmitting appropriate signals from a source, external to the body, which after being received in the HTS may be decoded and, when found to be proper, may be supplied to the memory to replace a corresponding, previously stored, parameter in the memory. Since the manner of changing parameters in a memory does not form part of this invention, it will not be described in any further detail.

As is appreciated by those familiar with the art, all memories can be classified as either volatile or non-volatile. A non-volatile memory is one in which the stored parameters are not affected by changes of the voltage which is supplied to the memory from a power source, e.g., a battery, which powers the memory. On the other hand, a volatile memory is one which can be relied upon as operating properly only when the voltage which is supplied thereto does not fall below an appropriate level. If however, the voltage from the power source falls below such a level, any parameter stored in the memory can no longer be relied upon since it may have changed, i.e., destroyed, when the voltage to the memory was insufficient for its appropriate operation.

In an HTS with a memory which stores parameters which in turn control the operation of the HTS, e.g., the properties of the stimulating signals, since the patient's safety in most instances depends on the properness of the stimulating pulses, it is paramount to insure that any or all of the stored parameters do not change in an arbitrary manner due to memory power failure. Such changes may endanger the patient's life. One way which this may be accomplished is to store the parameters in a non-volatile memory. If the parameters are to be stored in a volatile memory, some means must be provided to either protect the memory power supply and/or, if this cannot be done, to reset the memory to prevent dangerous stimulating regimes. Such means are hereinafter referred to as the memory protect means or circuit.

SUMMARY OF THE INVENTION

In one embodiment of the present invention the memory protect means includes circuitry which senses both the voltage across the battery and the voltage, which is supplied to power the memory. The voltage which powers the memory may be from a voltage regulator up converter, which is powered by the battery. When the voltage across the battery falls below a preselected level, except for the memory and the circuits which control the supply of power to the memory, all of the HTS circuits which draw power, including the pulse generator which provides stimulating pulses, as a function of the parameters in the memory, and the biotelemetry transmitter, are disconnected from the battery and thereby disabled. Thus, no stimulating pulses are supplied to the patient and only the memory remains connected to the battery through its power controlling circuitry. As a result, the battery life for powering only the memory is increased.

If, therefore, the battery is recharged by power from an external source, when the battery level rises to a sufficiently high level, the rest of the circuits are again connected and enabled. On the other hand, if the battery is not recharged, and the memory continues to drain power from the battery, when the voltage to the memory falls below a safe level, which is assumed to be necessary to safely retain the parameters in the volatile memory, the parameters can no longer be relied upon. Since the pulse generator has previously been disconnected, the fact that the parameters can no longer be relied upon does not affect the safety of the patient. Thereafter, when the battery is recharged, and when the memory is again powered by sufficient voltage, the memory is loaded with preselected parameters from a memory reset source in the HTS, e.g., a read only memory (ROM). These parameters are chosen so that thereafter when the pulse generator is reactivated the parameters, present in the memory, are of preselected values, which result in the generation of safe stimulating pulses from the pulse generator. Once the battery voltage exceeds the desired level, all the rest of the circuits are again reactivated. The parameters which have been loaded in the memory remain therein until subsequently other parameters from an external source are received by the HTS and are stored in the memory.

The novel features of the invention are set forth with particularity in the appended claims. The invention will best be understood from the following description when read in conjunction with the accompanying drawings.

BRIEF DESCRIPTION OF THE DRAWINGS

FIG. 1 is a general block diagram of an HTS with a rechargeable battery, a parameter-storing memory and the memory protect circuit of the present invention;

FIG. 2 is a diagram of the HTS with the novel memory protect circuit shown in greater detail; and FIG. 3 is a multiline waveform diagram useful in explaining the memory protect circuit shown in FIG. 2.

DESCRIPTION OF THE PREFERRED EMBODIMENTS

Attention is first directed to FIG. 1 which is a simplified block diagram of an HTS with the memory protect circuits of the present invention. The invention will be described in conjunction with a rechargeable battery.

In FIG. 1 the implantable HTS is represented by 10, and includes all the circuitry to the right of numeral 12, which designates a patient's skin. The HTS includes a battery 15, one end of which is connected to reference potential, e.g., circuit ground. The battery 15 is the source of power in the HTS. Circuits may be connected directly to the battery or to one or more up and/or down converters which are powered by the battery. To simplify FIG. 1, only one converter, an up converter 16, is shown. Its function is to provide a higher output voltage than that supplied thereto by battery 15. For explanatory purposes it is assumed that the battery 15, when fully charged, provides an output voltage of at least 1.2 v. and as long as the battery voltage is not less than 1.0 v the output voltage of the up converter is 4.0 v. As the battery voltage drops below 1.0 the voltage from converter 16 decreases from 4.0 v. It is further assumed that the volatile memory 20 in the HTS is powered by the up converter 16 and requires a voltage of not less than 3.4 v for safe operation.

As shown in FIG. 1 the output voltage of the converter 16 on line 18 is applied directly to memory 20. For explanatory purposes various HTS circuits, which do not form part of this invention, are lumped into two groups. One group is assumed to require a low voltage, such as that provided directly by the battery 15. This group is represented by low voltage circuits 22, which are connected through a normally closed switch S1 to the battery. S1 is shown in the open position. The other group of circuits is represented by high voltage circuits 24, shown connected to the higher output voltage of converter 16 through a switch S2. The latter is also normally closed, though shown in the open position.

The switches S1 and S2 are controlled by the memory protect circuit (MPC) 25 to which the present invention is directed. MPC 25 is supplied with the voltages from battery 15 and converter 16. In addition it is shown connected to a battery charging circuit 27, whose function is to recharge the battery when recharging energy is received from a source, external to the patient's body. For explanatory purposes, the HTS 10 is assumed to include an energy-receiving coil 28 into which energy may be coupled through the skin 12 from an energy-transmitting coil 31, which is driven by an external unit 30. Energy may be coupled by magnetic induction, by RF, and by any other known techniques, such as light, current conduction and the like. Techniques for coupling energy into an implanted device through the body skin are well known. Since the recharging of battery 15 from an external source does not form part of the invention, it will not be described in any detail.

It is sufficient to state that in the arrangement shown in FIG. 1, the battery recharging circuit 27 supplies a signal to MPC 25, via line 32, to indicate when battery recharging takes place, for purposes to be explained hereinafter. The MPC 25, based on the inputs thereto, controls switches S1 and S2 and the memory 20 as will be explained hereafter in conjunction with the voltage levels of battery 15 and converter 16, as hereinbefore assumed. To complete the description of FIG. 1, therein, an external coded parameter transmitter T1 and a receiver decoder R which forms part of the implanted HTS are shown. Briefly, the transmitter T is used to transmit coded parameters to receiver/decoder R. When decoded and found to be proper they are stored in memory 20. Such transmission is similar to transmitting any codes in a data transmission system for use, e.g., storage in a memory. Since this aspect does not form part of the invention, it will not be described hereafter.

Attention is directed to FIG. 2 which is similar to FIG. 1, except that the MPC 25 is shown in greater detail, and to FIG. 3, which is a multiline waveform diagram. As shown in FIG. 2, MPC 25 is assumed to incorporate a low voltage indicator (LVI) 35 which monitors the voltage across battery 15. Its function is to produce a high output as represented by 37 in line b of FIG. 3, whenever the voltage across the battery 15 is not less than 1.1 v. Once the battery voltage drops below 1.1 v the LVI output goes low, as represented by 38 (line b of FIG. 3). As will be pointed out hereinafter the LVI output returns to a high level only when the battery voltage reaches again 1.1 v only as a result of battery recharging.

Similarly, a high voltage indicator (HVI) 40, which senses the output voltage of the up converter 16, is included. The function of HVI 40 is to produce a high output, as represented by 41 in line d of FIG. 3, as long as the output voltage of the up converter 16, which under normal operation provides an output voltage of 4 v, is not less than 3.4 v. When the voltage from the converter 16 drops below 3.4 v, the output level of HVI 40 goes low, as represented by 43 in line d of FIG. 3. In this figure, lines a and c are used to diagram the output voltages of the battery 15 and the up converter 16, respectively.

Thus, LVI 35 can be viewed as a comparator which provides a low output when the battery voltage drops below 1.1 v. Once the output goes low it returns to high only when the battery voltage returns to 1.1 v as a result of battery charging, which is indicated by a signal on line 32. HVI 40 can also be viewed as a comparator. Its output is high as long as its input from converter 16 is not less than 3.4 v.

Let it be assumed that at some point in time the output of the battery 15 is not less than 1.2 v, i.e., the battery is fully charged. Therefore, the output voltage of the up converter 16 is 4 v and the HTS operates normally. Let is also be assumed that the battery 15 has not been recharged as required and that due to its power drainage its output voltage starts dropping. At time $t_1$ (see FIG. 3) when the voltage is assumed to have dropped to below 1.1 v, the LVI 35 output goes low (38 in line b). With the LVI output low, the normally closed switches S1 and S2 open up. Preferably the output of LVI 35 is supplied to the switches through a delay D, whose function will be described hereinafter. Consequently, both the low voltage circuits 22 and the high voltage circuits 24 are separated from the battery 15 and the converter 16, respectively. Only the memory 20 remains connected to the output of the up converter 16.

It should therefore be apparent that since the circuits 22 and 24 are disconnected from the battery and the converter they no longer drain any of the battery power. Only the memory 20 remains connected to the converter and therethrough drains some of the power of the battery 15. Since at this point in time the output of the battery is assumed to be sufficiently high so that the output of the up converter is above 3.4 v the memory is supplied with sufficient voltage to safely retain the parameters which are stored therein.

It is assumed that circuits 22 and 24, include a pulse generator which provides stimulating pulses to the patient as a function of the parameters in the memory. Thus, once these circuits 22 and 24 are disconnected the HTS does not provide any stimulating pulses to the patient. However, the stored parameters in the memory remain undisturbed. The absence of such pulses should alert the patient that something is wrong with the HTS and possibly alert him to the fact that the battery has not been recharged, as required.

It should further be pointed out that when the HTS circuits 22 and 24 are disconnected from draining battery power and only the memory remains powered by the battery, some rise in the battery output voltage may be experienced, as indicated by numeral 45 in the battery voltage waveform in line a of FIG. 3. In practice the battery voltage may even rise above 1.1 v. However, since such rise is not due to the recharging of the battery, but rather due to the separation of previously power-draining circuits therefrom, the output level of the LVI remains low (see line b) and therefore the switches S1 and S2 remain open.

For explanatory purposes, let it further be assumed that the battery 15 has not been recharged and, therefore, its voltage keeps dropping, due to power draining by the memory only, so that at time $t_2$ the battery voltage drops below 1 v. As previously assumed, when this occurs the output of the up converter 16 starts to drop from its previous level of 4 v, as represented by 46 in line c of FIG. 3. However, as long as the output voltage of the up converter 16 is not less than 3.4 v nothing happens. In the particular diagram, shown in FIG. 3, it is assumed that battery recharging starts at some point between time $t_2$ and time $t_3$, and that at time $t_3$ the voltage of the battery rises above 1 v. Consequently, the output voltage of the converter rises to and stays at 4 v. Then at time $t_4$ when the output voltage of the battery reaches 1.1 v, since this rise is due to battery recharging, as indicated by a signal on line 32, the output of the LVI 35 goes high. Thus, switches S1 and S2 are closed by a signal assumed to be supplied thereto from the LVI via line 48. Once switches S1 and S2 are closed, all the circuits are again connected in the HTS and are once more powered by the voltage from battery 15 or by the output voltage from the up converter 16.

The low to high transition of the LVI output causes a flip flop (FF) 42 to be reset, which is assumed to have been initially in the reset state. Consequently, the Q output of FF 42 is low. The function of FF 42 will be described later. Also, the output of LVI 35 is supplied to one output of an And gate 44 to which the Q output of FF 42 is also applied.

Let it further be assumed that again a long period elapses between charging operations, represented in FIG. 3 by the period between $t_4$ and $t_5$. At time $t_5$ (see FIG. 3) the battery voltage is assumed to drop below 1.1 v. Thus, the output of LVI 35 again goes low, causing the circuits 22 and 24 to become separated by means of switches S1 and S2, which are driven to their open state, and thereby are disconnected from further draining the battery. At time $t_6$, when the output voltage of the battery starts to drop below 1 v, the output voltage of the up converter 16 also starts to drop from its value of 4 v. As the battery voltage keeps dropping, the output voltage of the up converter also drops.

For explanatory purposes, it is assumed that at time $t_7$ the output voltage of the up converter drops below 3.4 v. As a result the output of HVI 40 goes low (as indicated by 43 on line d of FIG. 3). At this point, since the voltage applied to the memory 20 is less than is necessary for safe operation of the memory, the parameters, which are stored in it, can no longer be relied upon. However, at this point in time all the rest of the circuits (22 and 24), some of which may be operating as a function of the parameters in the memory, have been previously (at time $t_5$) disconnected from the battery and the up converter. Thus, they are inoperative. Consequently, the fact that the parameters in the memory 20 may change, as a result of the memory being supplied with a voltage of less than 3.4 v, is unimportant, since the circuits, whose operation depends on the parameters in the memory, are themselves inoperative. Since memory 20 remains connected to the up converter, even though the voltage therefrom has dropped below 3.4 v, the memory keeps draining the battery power. The battery voltage and that of the up converter keep dropping.

For explanatory purposes, let it further be assumed that when the voltage across the battery 15 drops to 0 v the output voltage of the up converter 16 is likewise 0 v. This condition is assumed to exist in the particular example until the patient at some point after time $t_7$ and before time $t_8$ causes the battery 15 to be recharged by supplying energy to the recharging circuit 27 from an external source. As the battery is being recharged and its voltage starts to rise from 0 v the output of the up converter 16 also rises. In the example it is assumed that at time $t_8$ the converter output voltage reaches 3.4 v, which is assumed to be the minimum voltage needed to power the memory. At this point in time the output of the HVI 40 goes high. The low to high transition of the output of HVI 40 is assumed to set FF 42, and therefore its Q output goes high. However, since at this point in time the LVI output is low, And gate 44 is not enabled, and therefore its output remains low.

It is further assumed that the battery continues to be recharged and that at time $t_9$ it is assumed to reach 1 v, and therefore the voltage output of up converter 16 reaches 4 v. At time $t_{10}$ the battery voltage is assumed to reach 1.1 v. Since this is due to battery recharging, as indicated by the signal supplied to LVI 35 from the recharging circuit 27 via line 32 the LVI output goes high. Since at this point in time the Q output of FF 42 is high, both inputs to And gate 44 are high. Therefore, the gate's output goes high.

The low to high transition of the output of And gate 44 may be used in different ways to load the memory 20 with preselected parameters. These parameters are chosen so that when subsequently the various circuits are re-enabled the parameters in the memory are of such values so that the pulse generator produces only safe stimulating pulses for the patient. One way that this may be accomplished is to use the low to high transition of the output of And gate 44 to simply reset each of the parameters in the memory 20 to an all 0 state. Circuit means can be included in the pulse generating circuitry so that with all parameters in the 0 state the magnitude, frequency and duration of the various stimulating pulses are safe for the patient.

Another way that the low to high transition of the output of And gate 44 may be used is to activate a non-volatile ROM 50 which stores preselected safe parameters. When ROM 50 is activated the safe parameters, stored therein, are loaded into memory 20. Clearly other techniques may be used to utilize the low to high transition in the output of And gate 44 to load the memory 20 with preselected known parameters. For explanatory purposes, in FIG. 2 the output of And gate 44 is shown as being supplied to the ROM 50, which in turn is shown connected to the memory 20 to supply the parameters thereto only when activated by a high output of And gate 44. It should be pointed out that the low to high transition of the output of LVI 35 at time $t_{10}$ also resets FF 42. The circuitry should include sufficient delay to insure that the resetting of FF 42 occurs after the And gate 44 was enabled in order to insure that the output of And gate 44 undergoes the low to high transition before FF 42 is reset. Also, delay D in line 48 provides sufficient delay to insure that switches S1 and S2 are closed only after memory 20 is reset with safe parameters.

In the foregoing description, the memory protect circuitry (MPC) 25 has been described in connection with an arrangement in which it is necessary for the output of HVI 40 to go high first before the output of LVI 35 goes high. It should be clear that the invention is not intended to be limited thereto. For example, those skilled in the art may design the MPC 25 so that both LVI 35 and HVI 40 have to have their outputs go from low to high before the memory 20 is loaded with the preselected parameters and switches S1 and S2 are closed. The point that should be kept in mind is that in accordance with the present invention, once the voltage to the memory 20 drops below a safe level for the proper memory operation (e.g., 3.4 v) the parameters stored therein can no longer be relied upon. Thus, when subsequently the voltage to the memory is increased to a level at least sufficient for the memory's proper operation, preselected parameters are loaded into the memory. These parameters are subsequently used when the rest of the HTS circuitry is reconnected to the powering sources, i.e., when switches S1 and S2 are closed, in order to assure that the circuit produce stimulating pulses which are safe for the patient.

It should be apparent that these stimulating pulses may have, and often do have, properties such as frequency, amplitude and width which differ from those which were originally chosen by the doctor by the loading of the memory 20 with parameters transmitted to the HTS from transmitter T. However, the properties of the stimulating pulses which are produced in response to those parameters which were loaded into memory 20 when the memory is reset, are such as to insure the patient's safety, which is of paramount importance.

From the foregoing, it should thus be apparent that the arrangement is particularly advantageous in order to protect a patient from being stimulated by stimulating pulses produced in response to other than known safe parameters. These parameters may be either those which have been previously transmitted to the HTS under the command of a doctor, or those preselected parameters which have been loaded into the memory only after the voltage to the memory has reached a sufficient level necessary to operate the memory. This arrangement prevents the activation of the pulse generator circuitry in the HTS from being controlled by unknown parameters generated from the volatile memory once it has been underpowered.

Briefly, in the embodiment hereinbefore described in which the battery is assumed to be of a type rechargeable by a recharging circuit to which energy is suppliable from an external source, if the recharging has not taken place when required, and the battery voltage starts to drop below a safe value, for example 1.1 v, all the circuits except the memory are disconnected from the battery (or the up converter which is in turn powered by the battery). Thus, once all the circuits except the memory, are disconnected, only the memory remains connected to and drains power from the battery. In practice the amount of current drained by the memory is considerably smaller than that which is drained by the various HTS circuits, particularly the pulse generator and any amplifiers connected thereto. Consequently, the period during which the voltage to the memory remains sufficiently high to insure the proper operation of the memory and therefore insures the safety of the parameters previously stored therein, is considerably longer, as compared with the period, which would be rather short, if all circuits remained connected to the battery which has not been recharged.

In the particular example, it was assumed that once the switches S1 and S2 open when the voltage drops below 1.1 v, they remain open until the voltage from the battery exceeds the selected level as a result of recharging only. Furthermore, in the particular example, it was pointed out that once the voltage to the memory dropped below a level, necessary for its safe operation, when subsequently the voltage thereto reaches at least the level necessary for its safe operation and the battery has been recharged to a desired level, preselected parameters are loaded into the memory for use by the other HTS circuitry, such as the pulse generator when the latter is again connected to the powering source, when switches S1 and S2 are closed.

The novel features of the invention are set forth with particularity in the appended claims. The invention will best be understood from the following description when read in conjunction with the accompanying drawings.

What is claimed is:

1. In a device-implantable in a human body for performing preselected functions therein the device including circuit means powered by power means and further including memory means for storing a plurality of parameter values, means for applying said parameter values to said circuit means to control operation of the latter as a function of the parameter values, an arrangement comprising:
   sensing means for sensing voltage applied by said power means to said memory means; and
   resetting means responsive to said sensing means for resetting said memory means to store preselected parameter values after said sensing means sensed that the voltage to said memory means first dropped below a preselected level and thereafter was not less than said preselected level.

2. An arrangment as described in claim 1 wherein said power means comprises a rechargeable battery and said circuit means include recharging means responsive to energy transmitted thereto from a source, external to said patient, for recharging said battery.

3. In a device implantable in a human body, the device including circuit means and memory means, said memory means storing a plurality of parameters, means for applying said parameters to said circuit means, to control the operation thereof, said device further including power means for powering said circuit means and said memory means, and recharging means for recharging said power means with energy received from a source external to the human body, an arrangement comprising:
   control means, including means for sensing the voltage provided by said power means, for disconnecting said circuit means from said power means when the voltage, provided by said power means, drops to a first level, and for reconnecting said circuit means to said power means only when the voltage level from said power means reaches at least said first level, as a result of said power means being recharged by said recharging means.

4. A device as recited in claim 3 wherein the control means further includes means for resetting said memory means with preselected parameters, once the voltage applied to said memory first dropped below a preselected level and thereafter increased to at least said preselected level.

5. A device as recited in claim 4 wherein said control means include means for reconnecting said circuit means to said power means when the voltage therefrom first dropped, so that the voltage to said memory means dropped below said preselected level, only after said memory means are reset and the voltage from said power means reached said first level, as a result of the power means being recharged by said recharging means.

6. In a device implantable in the human body for performing preselected functions therein the device including circuit means powered by power means and further including memory means for storing a plurality of parameter values, means for applying said parameter values to said circuit means to control operation of the latter as a function of the parameter values, an arrangement comprising:
   control means including sensing means for sensing the voltage provided by said power means, and disconnecting means for disconnecting said circuit means from said power means when the voltage therefrom falls below a first level, said power means comprising a rechargeable battery and said device includes recharging means responsive to energy transmitted thereto from a source, external to said patient, for recharging said battery and for providing a control signal which is indicative of battery recharging by said recharging means, said disconnecting means comprising switch means, and reconnecting means, responsive to said control signal for reconnecting previously disconnected circuit means, only when the voltage level from said battery reaches again said first level and said control signal is received from said recharging means.

7. A device as described in claim 6 wherein said memory means is of the volatile type, and said device further includes means for resetting said memory means to store preselected parameter values after the voltage to said memory means first dropped below a preselected level and thereafter was not less than said preselected level.

8. A device as described in claim 7 wherein said reconnecting means include means for reconnecting said circuit means to said power means when said voltage to said memory means first dropped below said preselected level only after said resetting means reset said memory means.

* * * * *